(12) United States Patent
Holoshitz et al.

(10) Patent No.: US 9,725,484 B2
(45) Date of Patent: Aug. 8, 2017

(54) METHODS AND COMPOSITIONS FOR THE TREATMENT OF BONE REMODELING DISORDERS

(71) Applicants: THE REGENTS OF THE UNIVERSITY OF MICHIGAN, Ann Arbor, MI (US); YISSUM RESEARCH DEVELOPMENT COMPANY OF THE HEBREW UNIVERSITY OF JERUSALEM, LTD, Jerusalem (IL)

(72) Inventors: Joseph Holoshitz, Ann Arbor, MI (US); Song Ling, Ypsilanti, MI (US); Chaim Gilon, Jerusalem (IL); Amnon Hoffman, Jerusalem (IL)

(73) Assignees: THE REGENTS OF THE UNIVERSITY OF MICHIGAN, Ann Arbor, MI (US); YISSUM RESEARCH DEVELOPMENT COMPANY OF THE HEBREW UNIVERSITY OF JERUSALEM, LTD., Jerusalem (IL)

( * ) Notice: Subject to any disclaimer, the term of this patent is extended or adjusted under 35 U.S.C. 154(b) by 0 days.

(21) Appl. No.: 14/770,276

(22) PCT Filed: Feb. 24, 2014

(86) PCT No.: PCT/US2014/018032
§ 371 (c)(1),
(2) Date: Aug. 25, 2015

(87) PCT Pub. No.: WO2014/130949
PCT Pub. Date: Aug. 28, 2014

(65) Prior Publication Data
US 2016/0002295 A1    Jan. 7, 2016

Related U.S. Application Data

(60) Provisional application No. 61/768,807, filed on Feb. 25, 2013.

(51) Int. Cl.
| | | |
|---|---|---|
| *A61K 38/12* | (2006.01) | |
| *C07K 7/56* | (2006.01) | |
| *C07K 7/06* | (2006.01) | |
| *A61K 38/00* | (2006.01) | |

(52) U.S. Cl.
CPC ............. *C07K 7/56* (2013.01); *A61K 38/12* (2013.01); *C07K 7/06* (2013.01); *A61K 38/00* (2013.01)

(58) Field of Classification Search
None
See application file for complete search history.

(56) References Cited

U.S. PATENT DOCUMENTS

| 7,074,893 B2 | 7/2006 | Holoshitz et al. |
|---|---|---|
| 7,208,154 B2 * | 4/2007 | Holoshitz .............. A61K 38/10 424/178.1 |
| 2006/0014680 A1 | 1/2006 | Xu et al. |

FOREIGN PATENT DOCUMENTS

| CA | 2230861 | 3/1997 |
|---|---|---|
| WO | 2011024175 A1 | 3/2011 |

OTHER PUBLICATIONS

Naveh et al (Bioorganic & Medicinal Chemistry Letters 22 (2012) 493-496).*
International Search Report dated May 22, 2014, of Application No. PCT/US2014/018032 Filed Feb. 24, 2014, (19 pages).
Bromley et al., "Histopathology of the rheumatoid lesion. Identification of cell types at sites of cartilage erosion." Arthritis Rheum. Aug. 1984;27(8):857-63.
De Almeida et al., "Immune dysregulation by the rheumatoid arthritis shared epitope." J Immunol. Aug. 1, 2010;185 (3):1927-34.
Fridman et al., "Selective inhibition of JAK1 and JAK2 is efficacious in rodent models of arthritis: preclinical characterization of INCB028050." J Immunol. May 1, 2010;184(9):5298-307.
Furst et al., "The risk of infections with biologic therapies for rheumatoid arthritis." Semin Arthritis Rheum. Apr. 2010;39(5):327-46.
Gonzales-Gay et al., "Influence of human leukocyte antigen-DRB1 on the susceptibility and severity of rheumatoid arthritis." Semin Arthritis Rheum. Jun. 2002;31(6):355-60.
Gravallese et al., "Synovial tissue in rheumatoid arthritis is a source of osteoclast differentiation factor." Arthritis Rheum. Feb. 2000;43(2):250-8.
Gregersen et al., "The shared epitope hypothesis. An approach to understanding the molecular genetics of susceptibility to rheumatoid arthritis." Arthritis Rheum. Nov. 1987;30(11):1205-13.
Holoshitz et al. "An HLA-DRB1-coded signal transduction ligand facilitates inflammatory arthritis: a new mechanism of autoimmunity." J Immunol. Jan. 1, 2013;190(1):48-57.
Holoshitz et al., "A role for calreticulin in the pathogenesis of rheumatoid arthritis." Ann N Y Acad Sci. Oct. 2010;1209:91-8.
Jawaheer et al., "Homozygosity for the HLA-DR shared epitope contributes the highest risk for rheumatoid arthritis concordance in identical twins." Arthritis Rheum. May 1994;37(5):681-6.
Kotake et al., "IL-17 in synovial fluids from patients with rheumatoid arthritis is a potent stimulator of osteoclastogenesis." J Clin Invest May 1999;103(9):1345-52.
Ling et al., "Activation of nitric oxide signaling by the rheumatoid arthritis shared epitope." Arthritis Rheum. Nov. 2006;54(11):3423-32.
Ling et al., "Citrullinated calreticulin potentiates rheumatoid arthritis shared epitope signaling." Arthritis Rheum. Mar. 2013;65(3):618-26.
Ling et al., "The rheumatoid arthritis shared epitope increases cellular susceptibility to oxidative stress by antagonizing an adenosine-mediated anti-oxidative pathway." Arthritis Res Ther. 2007;9(1):R5.

(Continued)

*Primary Examiner* — James H Alstrum Acevedo
*Assistant Examiner* — Sergio Coffa
(74) *Attorney, Agent, or Firm* — Casimir Jones, SC (57) ABSTRACT

The present invention relates to methods and compositions for treating disease related to disorders of bone remodeling. In particular, the present invention relates to compositions and methods for treating rheumatoid arthritis.

15 Claims, 6 Drawing Sheets

(56) References Cited

OTHER PUBLICATIONS

Ling et al., "The rheumatoid arthritis shared epitope triggers innate immune signaling via cell surface calreticulin." J Immunol. Nov. 1, 2007;179(9):6359-67.

Mattey et al., "Independent association of rheumatoid factor and the HLA-DRB1 shared epitope with radiographic outcome in rheumatoid arthritis." Arthritis Rheum. Jul. 2001;44(7):1529-33.

Naveh et al., "Developing potent backbone cyclic peptides bearing the shared epitope sequence as rheumatoid arthritis drug-leads." Bioorg Med Chem Lett. Jan. 1, 2012;22(1):493-6.

Plant et al., "Patterns of radiological progression in early rheumatoid arthritis: results of an 8 year prospective study." J Rheumatol. Mar. 1998;25(3):417-26.

Sato et al., "Th17 functions as an osteoclastogenic helper T cell subset that links T cell activation and bone destruction." J Exp Med. Nov. 27, 2006;203(12):2673-82.

Shahrara et al., "TH-17 cells in rheumatoid arthritis." Arthritis Res Ther. 2008;10(4):R93.

Stump et al., "A highly selective, orally active inhibitor of Janus kinase 2, CEP-33779, ablates disease in two mouse models of rheumatoid arthritis." Arthritis Res Ther. Apr. 21, 2011;13(2):R68.

Weyand et al., "Disease mechanisms in rheumatoid arthritis: gene dosage effect of HLA-DR haplotypes." J Lab Clin Med. Sep. 1994;124(3):335-8.

William et al., "Discovery of the macrocycle (9E)-15-(2-(pyrrolidin-1-ypethoxy)-7,12,25-trioxa-19,21,24-triaza-tetracyclo[18.3.1.1(2,5).1(14,18)]hexacosa-1(24),2,4,9,14(26),15,17,20,22-nonaene (SB1578), a potent inhibitor of ianus kinase 2/fms-like tyrosine kinase-3 (JAK2/FLT3) for the treatment of rheumatoid arthritis." J Med Chem. Mar. 22, 2012;55(6):2623-40.

* cited by examiner

METHODS AND COMPOSITIONS FOR THE TREATMENT OF BONE REMODELING DISORDERS

The present application is a national phase application under 35 U.S.C. §371 of PCT International Application No. PCT/US2014/018032, filed on Feb. 24, 2014, which claims priority to U.S. Provisional Patent Application No. 61/768,807, filed Feb. 25, 2013, each of which are herein incorporated by reference in their entireties.

STATEMENT REGARDING FEDERALLY SPONSORED RESEARCH OR DEVELOPMENT

This invention was made with government support under GM088560 and AR059085 awarded by the National Institutes of Health. The government has certain rights in the invention.

FIELD OF THE INVENTION

The present invention relates to methods and compositions for treating disease related to disorders of bone remodeling. In particular, the present invention relates to compositions and methods for treating rheumatoid arthritis.

BACKGROUND

Rheumatoid arthritis (RA) is a chronic, systemic inflammatory disorder that may affect many tissues and organs, but principally attacks flexible (synovial) joints. It can be a disabling and painful condition, which can lead to substantial loss of functioning and mobility if not adequately treated.

The process involves an inflammatory response of the capsule around the joints (synovium) secondary to swelling (hyperplasia) of synovial cells, excess synovial fluid, and the development of fibrous tissue (pannus) in the synovium. The pathology of the disease process often leads to the destruction of articular cartilage and ankylosis (fusion) of the joints. Rheumatoid arthritis can also produce diffuse inflammation in the lungs, membrane around the heart (pericardium), the membranes of the lung (pleura), and white of the eye (sclera), and also nodular lesions, most common insubcutaneous tissue.

Although the cause of rheumatoid arthritis is unknown, autoimmunity plays a pivotal role in both its chronicity and progression, and RA is considered a systemic autoimmune disease. It is a clinical diagnosis made on the basis of symptoms, physical exam, radiographs (X-rays) and labs.

Various treatments are available. Non-pharmacological treatment includes physical therapy, orthoses, occupational therapy and nutritional therapy but these do not stop the progression of joint destruction. Analgesia (painkillers) and anti-inflammatory drugs, including steroids, are used to suppress the symptoms, while disease-modifying antirheumatic drugs (DMARDs) are required to inhibit or halt the underlying immune process and prevent long-term damage. In recent times, the newer group of biologics has increased treatment options. About 1% of the world's population has rheumatoid arthritis, women three times as often as men. Onset is most frequent between the ages of 40 and 50, but people of any age can be affected.

Additional treatments are needed.

SUMMARY OF THE INVENTION

The present invention relates to methods and compositions for treating disease related to disorders of bone remodeling. In particular, the present invention relates to compositions and methods for treating rheumatoid arthritis.

In some embodiments, the present invention provides cyclic DKCLA (SEQ ID NO: 1) peptides, derivatives, mimetics, conjugates or antagonists thereof for use in treating or preventing disorders of bone remodeling such as autoimmune disease (e.g., RA).

For example, in some embodiments, the present invention provides a composition comprising a cyclic DKCLA (SEQ ID NO: 1) peptide. In some embodiments, the peptide is cyclized by the linker where m and n are integers. In some embodiments, the peptide has the structure:

where m and n are integers (e.g., each independently 1, 2, 3, 4, 5, 6, 7, 8, 9, or 10). In some embodiments, for example, m is 4 and n is 4, m is 3 and n is 3, m is 6 and n is 4, m is 4 and n is 6, m is 6 and n is 2, m is 3 and n is 4, although other integers are or combinations of integers are contemplated. In some embodiments, the composition is a pharmaceutical composition (e.g., comprising a pharmaceutically acceptable carrier).

The present invention further provides the use of any of the aforementioned compounds in the treatment or prevention of a disease or condition associated with deregulated bone remodeling. In some embodiments, the composition prevents or treats bone destruction. In some embodiments, the present invention provides any of the aforemented compositions for use in the treatment or prevention of a disease or condition associated with deregulated bone remodeling. In some embodiments, the present invention provides the use of any of the aforementioned compounds for the manufacture of a medicament for treatment or prevention of a disease or condition associated with deregulated bone remodeling.

The present invention also provides a method of treating or preventing a disease or condition associated with deregulated bone remodeling, comprising administering any of the aforementioned compounds to a subject. In some embodiments, the subject has been diagnosed with an autoimmune disease. In some embodiments, the administration treats or prevents bone destruction. Examples of diseases related to bone remodeling include, but are not limited to, inflammatory, metabolic, pharmacologic endocrinologic, infectious, neopleastic, mecahnical and idiopathic diseases. For example, inflammatory: arthritis (e.g., rheumatoid arthritis), periodontal disease, psoriatic arthritis, reactive arthritis, gout, systemic lupus erythematosis (SLE), ankylosing spondylitic, osteoarthritis, etc.; metabolic: osteoporosis, anorexia nervosa; endocinologic: vitamin D deficiency, Cushing's syndrome, hyperparathyroidism; pharmacologic: corticosteroids, other drug-induced osteoporosis; infectious: osteomyelitis; neoplastic: bone metastasis, primary bone tumors, multiple myeloma, etc.; mechanical: bone fracture healing, post-surgical, prosthesis-associated bone damage, disuse, paralysis, bedridden conditions, low gravity, etc.; idiopathic: Paget's disease of bone, osteonecrosis.

Additional embodiments are described herein.

BRIEF DESCRIPTION OF THE DRAWINGS

FIG. 3 shows effects of cyclic DKCLA (SEQ ID NO: 1) compounds in vivo. A. HS(4-4)c Trp (administered ip weekly at a dose of 10 picograms per mouse) inhibits CIA. N=10 per group. P value was calculated using a paired Student t-test; B. Incidence curves of CIA mice treated with or without HS(4-4)c Trp; C. Representative micro-CT images of paws of CIA mice treated with (lower panel) or without (upper panel) HS(4-4)c Trp, 1 picogram per mouse; D. Representative histology sections of TRAP-stained tissues of the knee joint of mice treated with (right) or without (left) HS(4-4)c Trp. The white arrow in the left image points at OC-rich area, which is shown in larger magnification in the boxed image in the upper right corner; E. OCs were counted in the joints of CIA mice treated with (white bar) or without (black bar) HS(4-4)c Trp as above. N=5 per group. F&G. Inactive cDKCLA (SEQ ID NO: 1) analog HS(3-4)c Trp does not inhibit arthritis incidence or severity.

DEFINITIONS

As used herein, the term "disorders of bone remodeling" refers to any disease or disorder that has as a symptom or sign, a disorder or deregulation of bone remodeling. Bone remodeling (or bone metabolism) is a lifelong process where mature bone tissue is removed from the skeleton (a process called bone resorption) and new bone tissue is formed (a process called ossification or new bone formation). An imbalance in the regulation of bone remodeling's two sub-processes, bone resorption and bone formation, results in or is the result of a variety of disorders of, inflammatory, metabolic, pharmacologic endocrinologic, infectious, neopleastic, mechanical and idiopathic nature. Specific examples of disease related to bone remodeling include, but are not limited to, arthritis (e.g., rheumatoid arthritis), periodontal disease, psoriatic arthritis, reactive arthritis, gout, SLE, ankylosing spondylitic, osteoarthritis, osteoporosis, anorexia nervosa, vitamin D deficiency, Cushing's syndrome, hyperparathyroidism, corticosteroids, other drug-induced osteoporosis, osteomyelitis, bone metastasis, primary bone tumors, multiple myeloma, bone fracture healing, post-surgical, prosthesis-associated bone damage, disuse, paralysis, bedridden conditions, low gravity, Paget's disease of bone, and osteonecrosis.

As used herein, "one or more signs or symptoms of rheumatoid arthritis" (RA; rheumatoid arthritis) include tender, warm, swollen joints, usually affected in a symmetrical pattern. Other symptoms of RA include fatigue and occasional fever or malaise. Pain and stiffness lasting more than 30 minutes in the morning or after a long rest are also common symptoms of RA.

As used herein, "improved" means a reduction in the severity of the signs or symptoms of RA and a return towards normal function.

As used herein, "treatment" refers to a reduction of signs or symptoms, or to a reduction of side effects. Symptoms are "reduced" when the magnitude (e.g. intensity) or frequency of symptoms is reduced. In the case of RA, symptoms are reduced, for example, when the subject experiences less pain, a shorter duration of morning joint stiffness, and less swelling in the affected joints. It is not intended that the present invention be limited only to cases where the symptoms are eliminated. The present invention specifically contemplates treatment such that symptoms are reduced (and the condition of the subject is thereby "improved"), albeit not completely eliminated.

As used herein, "derivatives" or "analogues" of a peptide refers to a number of alterations in such peptides. In some embodiments, the derivatives comprise peptides with amino acid sequence changes. Such changes can be conservative amino acid substitutions amino acid deletions or amino acid insertions, provided that the shared epitope or shared epitope motif activity is substantially (50% or greater) retained. Analogues have amino acid analogues in place of the corresponding natural amino acids. Examples of such analogues include (but are not limited to) p-fluorophenylalanine (an analogue of phenylalanine) and ethionine and norleucine. Analogues also include incorporation of D-amino acids at particular points along the peptide chain. Derivatives and analogues may be conjugated.

As used herein "protease resistant peptides" refers to modified peptides with a reduced (e.g., relative to peptides without modification) susceptibility to protease digestion. For example, a protease resistant peptide may comprise a protecting group, or may comprise at least one D-amino acid. It is not intended that the present invention be limited to complete protease resistance. It is enough if susceptibility to protease digestion is reduced. In some embodiments, susceptibility to protease digestion is reduced, for example, 20%, 30%, 50%, 75%, 80%, 90% 95% or more relative to peptides without modification (e.g, as measured by an in vitro or in vivo protease assay).

As used herein, "synthetic peptide" refers to a peptide made by chemical or enzymatic synthetic procedures well known in the art. Synthetic shared epitope- and shared epitope motif-containing peptides, derivatives, analogues and mimetics are contemplated.

As used herein, "protecting groups" are those groups that prevent undesirable reactions (such as proteolysis) involving unprotected functional groups. Protecting groups can be added to the N-terminus, C-terminus or both of an shared epitope-containing or shared epitope motif-containing peptide. In one embodiment, the present invention contemplates that the protecting group is an acyl or an amide. In one embodiment, the acyl is acetate. In another embodiment, the protecting group is a benzyl group. In another embodiment, the protecting group is a benzoyl group. The present invention also contemplates combinations of such protecting groups.

As used herein, "biological activity" of peptides, derivatives or analogues, mimetics and antagonists refers to the ability of the peptides, derivatives or analogues, mimetics and antagonists (e.g., cyclic shared-eptiope antagonist peptides) to modulate signal transduction pathways or inhibit shared-epitope peptide activity. Such activity can be assayed by a number of techniques. For example, biological activity can be assayed in an in vitro cAMP-mediated assay for DNA repair following induction of DNA damage. Shared epitope-containing peptides inhibit DNA repair in such an assay. Biological activity of such peptides can also be determined by measuring intracellular cAMP levels or protein kinase A activation following application of said peptides to cells.

As used herein, the "N-terminus" of a peptide refers to the end of the peptide with a free amino group. Note that the N-terminus amino group does not necessarily have to be "free", for example, it may be involved in linking of moieties to the N-terminus in conjugates.

As used herein, the "C-terminus" of a peptide refers to the end with a free carboxyl group. Note that the C-terminus carboxyl group does not necessarily have to be "free", for example, it may be involved in linking moieties to the C-terminus in conjugates.

As used herein, "subject" refers to a human or animal.

As used herein, "single dosage" refers to a pharmaceutical composition of a formulation that is capable of achieving its intended effect in a single application or administration (e.g. once a day).

As used herein, "oral administration" or "orally" refers to the introduction of a pharmaceutical composition into a subject by way of the oral cavity (e.g., in aqueous liquid or solid form).

As used herein, "sublingual administration" or "sublingually" refers to the introduction of a pharmaceutical composition into a subject by application to the mucosal surface under the tongue (within the oral cavity) such that the composition is absorbed into the subject.

As used herein, "buccal administration" or "buccal" refers to the introduction of a pharmaceutical composition into a subject by application to the mucosal surface lining the cheek (within the oral cavity) such that the composition is absorbed into the subject.

As used herein, "intranasal administration" or "intranasally" refers to the introduction of a pharmaceutical composition within the nasal cavity.

As used herein, "respiratory inhalation" refers to the introduction of a pharmaceutical composition within the respiratory tract.

As used herein, "intrapulmonary delivery" refers comprises administration to the lung. Intrapulmonary delivery of pharmacologic agents to patients can be accomplished via aerosolization. Alternatively, the agent may be administered to the lung through a bronchoscope.

As used herein, "transdermal administration" or "transdermally" or "cutaneously" refers to the introduction of a pharmaceutical composition into a subject by application to the surface of the skin such that the composition is absorbed into the subject.

As used herein, "injection" or "standard injection" refers to the placement of a pharmaceutical composition into a subject (e.g., with a hypodermic needle). For example, such injection can be made subcutaneously, intravenously, intramuscularly, intracavernosally, etc.

As used herein, "intra-articular" injection refers to direct injection of a pharmaceutical composition into a joint (for example, in a method of treatment of RA).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "subject" refers to organisms to be treated by the methods of the present invention. Such organisms include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition associated with an autoimmune disease (e.g., RA).

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

DESCRIPTION OF THE INVENTION

The present invention relates to methods and compositions for treating disease related to disorders of bone remodeling. In particular, the present invention relates to compositions and methods for treating rheumatoid arthritis.

Osteoclast (OC)-mediated bone damage is a common, devastating outcome in rheumatoid arthritis (RA) (Bromley et al., 1984 Arthritis Rheum. 27: 857-863; Gravallese et al., 2000. Arthritis Rheum. 43: 250-258). Despite the advent of biologic agents, treating erosive RA remains a challenging endeavor, due to insufficient understanding of the mechanisms that specifically trigger RA disease onset and determine its severity. Most current and emerging drugs are targeted at generic immune-modulating pathways or inflammatory cytokines. As a result, drug failure and/or side effects are all too common.

While the pathogenesis of RA is not well understood, it has been long observed that the majority of RA patients carry HLA-DRB1 alleles coding a five amino acid sequence motif called the 'shared epitope' (SE) in the region 70-74 of the DRβ chain (Gregersen et al., 1987. Arthritis Rheum. 30: 1205-1213). The SE not only confers a higher risk for RA, but also increases the likelihood of developing a more severe disease. SE-coding HLA-DRB1 alleles are associated with earlier disease onset and more severe bone erosions (Gonzalez-Gay et al., 2002. Semin. Arthritis Rheum. 31: 355-360; Mattey et al., 2001. Arthritis Rheum. 44: 1529-1533; Plant et al., 1998 J. Rheumatol. 25: 417-426; Weyand et al., 1994. J. Lab. Clin. Med. 124: 335-338). Furthermore, there is evidence of gene-dose effect, where the extent of bone destruction in RA correlates positively with the number of SE-coding HLA-DRB1 alleles (Mattey et al., supra; Plant et al., supra; Weyand et al., supra).

SE functions as a signal transduction ligand that binds to cell surface calreticulin (CRT) in a strictly allele-specific manner and activates nitric oxide (NO)-mediated pro-oxidative signaling (Ling et al., 2006. Arthritis Rheum. 54: 3423-3432; Ling et al., 2007. Arthritis Res Ther 9: R5; Ling et al., 2007. The Journal of Immunology 179: 6359-6367; Ling et al., 2012 Arthritis Rheum.; De Almeida et al., 2010. The Journal of Immunology 185: 1927-1934; Holoshitz et al., 2010 Ann. N. Y. Acad. Sci. 1209: 91-98; U.S. Pat. Nos. 7,208,154; 7,074,893; each of which is herein incorporated by reference in its entirety). One of the functional consequences of SE ligand-activated signaling is expansion of IL-17-producing T (Th17) cells, both in vitro and in vivo (De Almeida et al., supra)).

Th17 cells are central players in arthritis pathogenesis (Shahrara et al., 2008 Arthritis Res Ther 10: R93). These cells have been previously shown to express high levels of the receptor activator for nuclear factor-κB (RANK) ligand (RANKL) and activate osteoclastogenesis (Sato et al., 2006 J. Exp. Med. 203: 2673-2682; Kotake et al., 1999 J. Clin. Invest. 103: 1345-1352). In previous studies, it was demonstrated that the SE ligand facilitates osteoclast (OC) differentiation in mouse and human cells in vitro and enhanced the differentiation of RAKL-expressing Th17 cells. When administered in vivo to mice with collagen-induced arthritis (CIA), the SE ligand increased joint swelling, synovial tissue OC abundance and erosive bone damage (Holoshitz et al., 2012, J. Immunol).

Given that the SE acts as a signal transduction ligand that directly contributes to arthritis severity, experiments described herein developed ways to inhibit this pathway. Experiments described herein describe the development of a peptidomimetic SE-antagonistic ligand (SEAL) with highly potent anti-osteoclastogenic and therapeutic effects in an experimental model of RA, CIA. These findings indicate that targeting the SE-activated pathway is a useful therapeutic strategy in RA.

The significance of the findings reported here relates to the fact that they provide direct evidence for the druggability of the SE-CRT pathway. Despite the advent of biologic agents, treating erosive RA remains a challenging endeavor. This reality is largely due to lack of sufficient understanding of the mechanisms that specifically trigger disease onset and determine its severity. Current treatment modalities, to the most part, target cytokines, their receptors, or other players in the final common pathway of the immune-driven inflammatory process. Due to their involvement in the 'downstream' segment of RA pathogenesis, those targets are often dispensable and/or not sufficiently specific. As a result, current treatment modalities are often ineffective and/or carry high rates of side effects, mainly infectious (Furst 2010. Semin. Arthritis Rheum. 39: 327-346). Experiments described herein indicate that targeting the SE-CRT pathway solves presently unmet therapeutic challenges in RA, by offering high potency, strict specificity, an 'upstream' effect, and a dual effect on OC and the immune system.

The compounds described here were found to be highly potent both in vitro and in vivo. For example, compound HS(4-4)c Trp competitively inhibited the binding of the SE ligand to its receptor CRT and blocked the SE signaling effects at low-pM concentrations. The inhibitory effect on OC differentiation, likewise, was seen at sub-to-low-pM concentrations. As a comparison, INCB028050, a JAK1/JAK2-selective small molecular inhibitor, has been recently reported to exert in vitro inhibition in rodent cells with IC50 values at the nM range (Fridman et al., 2010J. Immunol. 184: 5298-5307), which is a ~1000-fold lower potency than compound HS(4-4)c Trp described here. The in vivo effect of compound HS(4-4)c Trp, likewise, was much more potent than those of emerging new drugs. For example, the investigative small compounds INCB028050 (Fridman et al., supra), SB1518 (William et al., 2012 J. Med. Chem. 55: 2623-2640), or CEP-33779 (Stump et al., 2011 Arthritis Res Ther 13: R68) have all been shown to exert therapeutic efficacy in CIA at a mg/kg-range doses. By contrast, compound HS(4-4)c Trp described here achieved disease amelioration effects at ng/kg-range doses, e.g., at a 1,000,000-fold higher potency.

Another important aspect of the therapeutic approach described here is its specificity. The identification of the linear sequence DKCLA (SEQ ID NO: 1) as a potential SEAL was based on single amino acid substitutions made into the SE motif Q/R-K/R-x-x-A (SEQ ID NO: 2). DKCLA (SEQ ID NO: 1) is different from that motif by a single substitution from Gln (or Arg) to Asp. Asp in position 70 of the DRβ chain has been previously proposed to confer protection against RA (Gonzalez-Gay et al., 2002. Semin. Arthritis Rheum. 31: 355-360). Thus, it is contemplated that an N-terminal Gln is an important residue that determines SEAL effects. In addition to illustrating the role played by SEAL primary amino acid sequence, the data described herein demonstrate that secondary structure plays a major role as well. All compounds described here had an identical primary amino acid sequence, and differed in the lengths of their cyclization links only. Despite their primary sequence identity, however, those compounds demonstrated disparate potencies, with $IC_{50}$ values spanning over at least 6 orders of magnitude (Table 1). This finding further emphasizes the role of compounds conformation for optimal SEAL effect.

Targeting the SE-CRT pathway provides an additional advantage over the prevailing therapeutic paradigms, due to the unique role played by this pathway at an 'upstream' phase in RA pathogenesis. The SE is the single most significant risk factor for RA. It determines susceptibility, severity and even disease penetrance in monozygotic twins (Jawaheer et al., 1994 Arthritis Rheum. 37: 681-686). Thus, different from effector cytokines or enzymes involved in lymphocyte activation, this pathway is intimately involved in disease etiology and early genesis.

In addition, the compounds described herein address both immune and OC dysregulation and offer a dual therapeutic effect. To date, the focus of treatment modalities in the field has been on the immune and inflammatory systems, with an expectation that effective immune suppression or anti-inflammatory measures might indirectly prevent bone destruction. This study identified drugs that provides both autoimmune and anti-inflammatory effects.

I. Compounds

As described herein, embodiments of the present disclosure provide cyclic SE peptides for use in research, screening, and therapeutic applications. In some embodiments, peptide are cyclic SE antagonist or inhibitor peptides. In some embodiments, peptides comprise the sequence DKCLA (SEQ ID NO: 1). In some embodiments, peptides are cyclized via linkers. In some embodiments, peptides are cyclized by the linker where m and n are integers. For example, in some embodiments, the compound has the structure:

where m and n are integers. Table 1 shows activity of the compound with a variety of m and n values.

The present invention also provides methods of modifying and derivatizing the compositions of the present invention to increase desirable properties (e.g., binding affinity, activity, solubility and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In some embodiments, rational design methods are used to predict and model in silico ligand-receptor interactions prior to confirming results by routine experimentation.

In some embodiments, the present invention contemplates peptides that are protease resistant. In one embodiment, such protease-resistant peptides are peptides comprising protecting groups. In some embodiments, the present invention contemplates a peptide that is protected from protease degradation by N-terminal acetylation ("Ac") and C-terminal amidation. The acetylated and amidated shared epitope- or shared epitope motif-containing peptide is useful for in vivo administration because of its resistance to proteolysis.

In another embodiment, the present invention also contemplates peptides comprising their corresponding D-isomers. It is not intended that the present invention be limited to particular amino acids and particular D-isomers. This embodiment is feasible for all amino acids, except glycine; that is to say, it is feasible for all amino acids that have two stereoisomeric forms. By convention, these mirror-image structures are called the D and L forms of the amino acid. These forms cannot be interconverted without breaking a chemical bond. With rare exceptions, only the L forms of amino acids are found in naturally occurring proteins.

In other embodiments, peptides protected from protease degradation by both the use of protecting groups and substitution of L-amino acids with their corresponding D-isomers are contemplated. For example, a peptide comprising at least one D-amino acid can be acetylated and amidated as described above.

Synthesis of non-peptide compounds that mimic peptide sequences is also known in the art. Eldred et al. (*J. Med. Chem.* 37:3882 (1994)) describe non-peptide antagonists that mimic an Arg-Gly-Asp sequence. Likewise, Ku et al. (*J. Med. Chem.* 38:9 (1995)) give further elucidation of a series of such compounds. Such non-peptide compounds that mimic DKCLA (SEQ ID NO: 1) containing peptides are specifically contemplated.

The present invention also contemplates synthetic mimicking compounds that are multimeric compounds that repeat the relevant peptide sequences. In one embodiment of the present invention, it is contemplated that the relevant peptide sequence is DKCLA (SEQ ID NO: 1).

The present invention contemplates the design of peptide and nonpeptide mimetics based upon structural modeling of the DKCLA (SEQ ID NO: 1) and related peptides, high resolution experimental three dimensional imaging of DKCLA (SEQ ID NO: 1), conformational and binding site analysis of shared epitope- and calreticulin-inhibitory peptides, rational design of shared epitope- and calreticulin-inhibitory compounds, screening of combinatorial peptide libraries for shared epitope- and calreticulin-inhibitory constituents, and design of bio-stable shared epitope- and calreticulin-inhibitory peptide and nonpeptide mimetics. Certain of the compounds suitable for use in the present invention may exist as stereoisomers including optical isomers. The invention includes all stereoisomers and both the racemic mixtures of such stereoisomers as well as the individual enantiomers that may be separated according to methods that are well known to those of skill in the art. In certain embodiments, the compounds of the present invention do not comprise more than three naturally occurring amino acids, preferably no more than two naturally occurring amino acids, even more preferably no more than one naturally occurring amino acid.

Conjugates comprising the shared peptides described herein or analogues, derivatives, or mimetics linked to at least one additional moiety are also contemplated. The additional moiety may be a carrier molecule, to facilitate delivery of the conjugate to the appropriate target organ or tissue. In some embodiments, the conjugates are contemplated for delivery to the brain, for example, across the blood brain barrier. In other embodiments, the conjugates are contemplated for enhanced permeability for topical administration (for example, topical administration over a joint affected by rheumatoid arthritis).

A variety of carrier molecules are contemplated, and may vary, depending on the desired delivery or administration format. Among the carrier molecules contemplated are lipophilic or hydrophobic moieties, antibodies (and fragments thereof) and polyamines, although additional carrier molecules are also considered.

D. Routes of Administration and Formulations

The present invention is not limited by the method of introduction of the therapeutic compound to the body. Among other methods, the present invention contemplates administering cutaneously, orally, or by standard injection (e.g. intravenous).

The present invention also contemplates administering cyclic DKCLA (SEQ ID NO: 1) peptides, derivatives, mimetics, conjugates or antagonists to the patient intranasally or through respiratory inhalation. Formulations suitable for intranasal administration include ointments, creams, lotions, pastes, gels, sprays, aerosols, oils and other pharmaceutical carriers which accomplish direct contact between the compounds of the invention or a pharmaceutical composition comprising compounds of the invention and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all herein incorporated by reference. Formulations suitable for respiratory inhalation include ointments, creams, lotions, pastes, gels, sprays, aerosols, oils and other pharmaceutical carriers which accomplish direct contact between compounds of the invention or a pharmaceutical composition comprising compounds of the invention and the respiratory tract. Examples of pharmaceutical compositions administered through respiratory inhalation are described in U.S. Pat. No. 4,552,891 to Hu et al.; U.S. Pat. No. 5,869,479 to Kreutner et al., and U.S. Pat. No. 5,864,037 to Chasis et al., all herein incorporated by reference.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacologic agents to patients can be accomplished via aerosolization. Alternatively, the agent may be administered to the lung through a bronchoscope. Of course, the therapeutic agents may be investigated for their efficacy via other routes of administration, including parenteral administration.

While the present invention is not limited by the form of oral administration, aqueous and organic solutions of cyclic DKCLA (SEQ ID NO: 1) peptides, derivatives, mimetics, conjugates or antagonists are contemplated. Likewise, compounds of the invention can be associated with a solid pharmaceutical carrier for solid oral administration (i.e., in pill form). One skilled in the art is able to readily prepare such solid formulations, and in one embodiment, the inactive ingredients include croscarmellose sodium, hydroxypropyl methylcellulose, lactose, magnesium stearate, methocel E5, microcrystalline cellulose, povidine, propylene glycol and titanium dioxide.

Cyclic DKCLA (SEQ ID NO: 1) peptides, derivatives, mimetics, conjugates or antagonists may also be administered cutaneously in a carrier adapted for topical administration. Such carriers include creams, ointments, lotions, pastes, jellies, sprays, aerosols, bath oils, or other pharmaceutical carriers that accomplish direct contact between the compounds of the invention and the pore of the skin. In general pharmaceutical preparations may comprise from about 0.001% to about 10%, and preferably from about 0.01 to 5% by w/w of the active compound. In some cases it may be useful to dissolve the active compound in an appropriate solvent such as ethanol or DMSO (dimethylsulfoxide), and the like, to facilitate incorporation into a pharmaceutical preparation.

While the present invention is not limited by a specific method of introducing compounds of the invention by injection, injection of the compounds of the invention can be carried out by any conventional injection means (e.g., employing an hypodermic syringe and needle or a similar device such as the NovolinPen. sold by Squibb-Novo, Inc., Princeton, N.J., USA). This injection may be by the subject injecting him or herself or by another person injecting the patient.

Cyclic DKCLA (SEQ ID NO: 1) peptides, derivatives, mimetics, conjugates or antagonists can be introduced by injection in a physiologically acceptable composition. Such compositions are aqueous solutions that are physiologically acceptable for administration by injection. The physiologically acceptable carrier is selected such that it is not painful or irritating upon injection. The physiologically acceptable compositions will preferably be sterile at the time of administration by injection.

Among the physiologically acceptable compositions for use in the methods is physiological saline or phosphate buffered saline, in which compounds of embodiments of the present invention are dissolved or suspended, such that the resulting composition is suitable for injection. Such a physiologically acceptable composition can also include a non-irritant preservative, such as, e.g., benzalkonium chloride at 0.05% (w/v) to 0./2% (w/v).

While the present invention is not limited to the method of injecting compounds, in some embodiments, it is injected with a standard syringe. One skilled in the art would be capable of injecting compounds of the present invention with a carrier as described above.

In some embodiments (e.g. in a method of treating a subject with symptoms of RA), it is desirable that the compositions of the invention reach the affected joints. In some embodiments, this may be accomplished by cutaneous or transdermal application of pharmaceutical compositions comprising cyclic DKCLA (SEQ ID NO: 1) peptides, derivatives, mimetics, conjugates or antagonists directly to the skin over the affected joint. In other embodiments, delivery of the compounds to the affected joints may be by direct injection into the joint. The present invention specifically contemplates intra-articular injections in RA patients.

To perform an arthrocentesis, the specific area of the joint to be injected is palpated and is then marked, e.g., with firm pressure by a ballpoint pen that has the inked portion retracted. This will leave an impression that will last 10 to 30 minutes. (The ballpoint pen technique can also be used with soft tissue injection.) The area to be aspirated and/or injected should be carefully cleansed with a good antiseptic, such as one of the iodinated compounds. Then the needle can be inserted through the ballpoint pen impression.

Helpful equipment includes the following items: alcohol sponges; iodinated solution and surgical soap; gauze dressings (2×2); sterile disposable 3-, 10- and 20-ml syringes; 18- and 20-gauge, 1½-inch needles; 20-gauge spinal needles; 25-gauge, ⅝-inch needles; plain test tubes; heparinized tubes; clean microscope slides and coverslips; heparin to add to heparinized tubes if a large amount of inflammatory fluid is to be placed in the tube; fingernail polish to seal wet preparation; chocolate agar plates or Thayer-Martin medium; tryptic soy broth for most bacteria; anaerobic transport medium (replace periodically to keep culture media from becoming outdated); tubes with fluoride for glucose; plastic adhesive bandages; ethyl chloride; hemostat; tourniquet for drawing of simultaneous blood samples; and 1 percent lidocaine.

Knee.

The knee is the easiest joint to inject. The patient should be in a supine position with the knee fully extended. The puncture mark is made just posterior to the medial portion of the patella, and an 18- to 20-gauge, 1½-inch needle directed slightly posteriorly and slightly inferiorly. The joint space should be entered readily. On occasion thickened synovium or villous projections may occlude the opening of the needle, and it may be necessary to rotate the needle to facilitate aspiration of the knee when using the medial approach. An infrapatellar plica, a vestigal structure that is also called the ligamentum mucosum, may prevent adequate aspiration of the knee when the medial approach is used. However, the plica should not adversely affect injections or aspirations from the lateral aspect.

Shoulder.

Injections in the shoulder are most easily accomplished with the patient sitting and the shoulder externally rotated. A mark is made just medial to the head of the humerus and slightly inferiorly and laterally to the coracoid process. A 20- to 22-gauge, 1½-inch needle is directed posteriorly and slightly superiorly and laterally. One should be able to feel the needle enter the joint space. If bone is hit, the operator should pull back and redirect the needle at a slightly different angle.

The acromioclavicular joint may be palpated as a groove at the lateral end of the clavicle just medial to the shoulder. A mark is made, and a 22- to 25-gauge, ⅝- to 1-inch needle is carefully directed inferiorly. Rarely is synovial fluid obtained.

The sternoclavicular joint is most easily entered from a point directly anterior to the joint. Caution is necessary to avoid a pneumotharax. The space is fibrocartilaginous, and rarely can fluid be aspirated.

Ankle Joint.

For injections of the compounds of the present invention in the ankle joints, the patient should be supine and the leg-foot angle at 90 degrees. A mark is made just medical to the tibialis anterior tendon and lateral to the medial malleolus. A 20- to 22-gauge, 1½-inch needle is directed posteriorly and should enter the joint space easily without striking bone.

Subtalar Ankle Joint.

Again, the patient is supine and the leg-foot angle at 90 degrees. A mark is made just inferior to the tip of the lateral mallcolus. A 20- to 22-gauge, 1½-inch needle is directed perpendicular to the mark. With this joint the needle may not enter the first time, and another attempt or two may be necessary. Because of this and the associated pain, local anesthesia may be helpful.

Wrist.

This is a complex joint, but fortunately most of the intercarpal spaces communicate. A mark is made just distal to the radius and just ulnar to the so-called anatomic snuff box. Usually a 24- to 26-gauge, ⅝ to 1-inch needle is adequate, and the injection is made perpendicular to the mark. If bone is hit, the needle should be pulled back and slightly redirected toward the thumb.

First Carpometacarpal Joint.

Degenerative arthritis often involves this joint. Frequently the joint space is quite narrowed, and injections may be difficult and painful. A few simple maneuvers may make the injection fairly easy, however. The thumb is flexed across the palm toward the tip of the fifth finger. A mark is made at the base of the first metacarpal bone away from the border of the snuff box. A 22- to 26-gauge, ⅝ to 1-inch needle is inserted at the mark and directed toward the proximal end of the fourth metacarpal. This approach avoids hitting the radial artery.

Metacarpophalalangeal Joints and Finger Interphalangral Joints.

Synovitis in these joints usually causes the synovium to bulge dorsally, and a 24- to 26-gauge, ½ to ⅝-inch needle can be inserted on the either side just under the extensor tendon mechanism. It is not necessary for the needle to be interposed between the articular surfaces. Some prefer having the fingers slightly flexed when injecting the metacarpophalangeal joints. It is unusual to obtain synovial fluid. When injecting, a mix of the compounds of the present invention with a small amount of local anesthetic is also contemplated.

Metatarsophalangeal Joints and Toe Interphalangeal Joints.

The techniques are quite similar to those of the metacarpophalangeal and finger interphalangeal joints, but many prefer to inject more dorsally and laterally to the extensor tendons. Marking the area(s) to be injected is helpful as is gentle traction on the toe of each joint that is injected.

Elbow.

A technique preferred by many is to have the elbow flexed at 90 degrees. The joint capsule will bulge if there is inflammation. A mark is made just below the lateral epicondyle of the humerus. A 22-gauge, 1 to 1½-inch is inserted at the mark and directed parallel to the shaft of the radius or directed perpendicular to the skin.

Hip.

This is a very difficult joint to inject even when using a fluoroscope as a guide. Rarely is the physician quite sure that the joint has been entered; synovial fluid is rarely obtained. Two approaches can be used, anterior or lateral. A 20-gauge, 3½-inch spinal needle should be used for both approaches.

For the anterior approach, the patient is supine and the extremity fully extended and externally rotated. A mark should be made about 2 to 3 cm below the anterior superior iliac spine and 2 to 3 cm lateral to the femoral pulse. The needle is inserted at a 60 degree angle to the skin and directed posteriorly and medially until bone is hit. The needle is withdrawn slightly, and possibly a drop or two of synovial fluid can be obtained, indicating entry into the joint space.

Many prefer the lateral approach because the needle can "follow" the femoral neck into the joint. The patient is supine, and the hips should be internally rotated—the knees apart and toes touching. A mark is made just anterior to the greater trochanter, and the needle is inserted and directed medially and sightly cephalad toward a point slightly below the middle of the inguinal ligament. One may feel the tip of the needle slide into the joint.

Temporomandibular Joint.

For injections, the temporomandibular joint is palpated as a depression just below the zygomatic arch and 1 to 2 cm anterior to the tragus. The depression is more easily palpated by having the patient open and close the mouth. A mark is made and, with the patient's mouth open, a 22-gauge, ½ to 1-inch needle is inserted perpendicular to the skin and directed slightly posteriorly and superiorly.

II. Methods of Treatment

Embodiments of the present disclosure provide compositions and methods for treating a variety of autoimmune disease, including but not limited to, rheumatoid arthritis (RA). In some embodiments, compounds (e.g., cyclic DKCLA (SEQ ID NO: 1) peptides, derivatives, mimetics, conjugates or antagonists) are administered to subjects diagnosed with RA. In some embodiments, the administration reduces or eliminates one or more symptoms of RA. In some embodiments, administration prevents or reverses bone damage caused by RA.

In some embodiments, compositions comprising cyclic DKCLA (SEQ ID NO: 1) peptides, derivatives, mimetics, conjugates or antagonists are administered once to an subject in need thereof. In other embodiments, compositions are administered on an ongoing, recurrent, or repeat basis (e.g., multiple times a day, once a day, once every 2, 3, 4, 5, or 6 days, once a week, etc.) for a period of time (e.g., multiple days, months, or weeks). Suitable dosages and dosing schedules are determined by one of skill in the art using suitable methods (e.g., those described in the experimental section below or known to one of skill in the art).

In some embodiments, the present invention provides methods of treating disorder characterized as involving deregulated bone remodeling. Examples include, but are not limited to, inflammatory, metabolic, pharmacologic endocrinologic, infectious, neoplastic, mechanical and idiopathic diseases. The following are representative examples for the above-mentioned categories:

Inflammatory: arthritis (e.g., rheumatoid arthritis), periodontal disease, psoriatic arthritis, reactive arthritis, gout, SLE, ankylosing spondylitic, osteoarthritis, etc.

Metabolic: Osteoporosis, anorexia nervosa

Endocinologic: vitamin D deficiency, Cushing's syndrome, hyperparathyroidism

Pharmacologic: Corticosteroids, other drug-induced osteoporosis

Infectious: osteomyelitis

Neoplastic: Bone metastasis, primary bone tumors, multiple myeloma, etc.

Mechanical: bone fracture healing, post-surgical, prosthesis-associated bone damage, disuse, paralysis, bedridden conditions, low gravity, etc.

Idiopathic: Paget's disease of bone, osteonecrosis

EXPERIMENTAL

The following examples serve to illustrate certain preferred embodiments and aspects of the present invention and are not to be construed as limiting the scope thereof.

Example 1

Materials and Methods
Reagents, Cells and Mice

Ficoll-Paque™, 4,5-Diaminofluorescein Diacetate (DAF-2 DA), 5-(and -6)-chloromethyl-2',7' dichlorodihydrofluorescein (CM-H2DCFDA), macrophage colony-stimulating factor (M-CSF), RANKL, denatured chicken collagen type II (CII), and complete Freund's Adjuvant (CFA) were purchased from previously listed sources. All other commercial reagents were purchased from Sigma (St Louis, Mo.). Linear peptides were synthesized and purified (>90%) as previously described (Ling et al., 2006 supra; Ling et al., 2007 Arthritis Res Ther 9: R5; Ling et al., 2007 The Journal of Immunology 179: 6359-6367; De Almeida et al., supra). Peptidomimetics were prepared by backbone cyclization (Kotake et al., 1999 J. Clin. Invest. 103: 1345-1352) of a 5mer peptide carrying the sequence DKCLA (SEQ ID NO: 1). Recombinant mouse CRT was purified as described (Ling and Holoshitz. 2007 The Journal of Immunology 179: 6359-6367).

Isolation of human peripheral blood mononuclear cells (PBMCs) and culture of M1 fibroblasts were previously described (Holoshitz et al., 2012, J. Immunol.). DBA/1 mice, 6 to 10 weeks old, were purchased from the Jackson Laboratory (Bar Harbor, Me.). Mice were maintained and housed at the University of Michigan-Unit for Laboratory Animal Medicine facility, and all experiments were performed in accordance with protocols approved by University of Michigan Committee on Use and Care of Animals.

In Vitro Assays

Surface plasmon resonance (SPR) and signal transduction assays were performed as previously described (Holoshitz et al., 2012; supra; Ling et al., 2010. PLoS ONE 5: e11703; Ling et al., 2012 Arthritis Rheum.). In vitro assays for OC differentiation, using primary bone marrow cells (BMCs) isolated from femurs and tibias, or PBMCs isolated from healthy blood donors were performed as previously described (Holoshitz et al., 2012; supra).

CIA Induction In Vivo Compound Administration Joint Tissue Studies and Imaging

DBA/1 mice (7-10 week old) were immunization as described (Holoshitz, 2012, J. Immunol.) with chicken CII in CFA. In brief, 50 µl of an emulsion containing 100 µg of CII in 25 µl of 0.05 M acetic acid and 25 µl of CFA was injected intradermally at the base of the tail. Mice were injected once per week intraperitoneally with either 1 or 10 pg (HS4-4)c Trp at in 50 μl of PBS. Arthritis severity was determined as previously described (Holoshitz, 2012, J. Immunol.), using a visual scoring system on a 4-point scale for each paw: 0=no arthritis, 1=swelling and redness confined to digits, 2=minor swelling and redness spreading from the digits to the distal paw, and 3=major swelling and redness extending proximally from the paw.

Limbs were dissected and decalcified in 10% EDTA for 14 days at 4° C. After decalcification, the specimens were processed for paraffin embedding and serial sectioned. The histological sections were deparaffinized, rehydrated and stained with hematoxylin and eosin (H&E), or for tartrate-resistant acid phosphatase (TRAP) activity using a commercial kit (Kamiya Biomedical Company, Seattle, Wash.). To determine OC abundance, TRAP-positive multinucleated cells were counted. Data represent mean±SEM of the total number of OCs in front and rear paws+knees. Bone damage was evaluated by radiography and micro-computed tomography (micro-CT) as previously described (Holoshitz, 2012, J. Immunol.).

Statistical Analysis

Data are expressed as mean±SEM from triplicate samples. All experiments were repeated at least 3 times. Unless otherwise stated, statistical analyses were performed using a 2-tailed Student's T-test (*, p<0.05; , p<0.01; *, p<0.001)

Results and Discussion

DKCLA (SEQ ID NO: 1)—a Short Linear Synthetic Peptide with SEAL Activity

Figure 1:
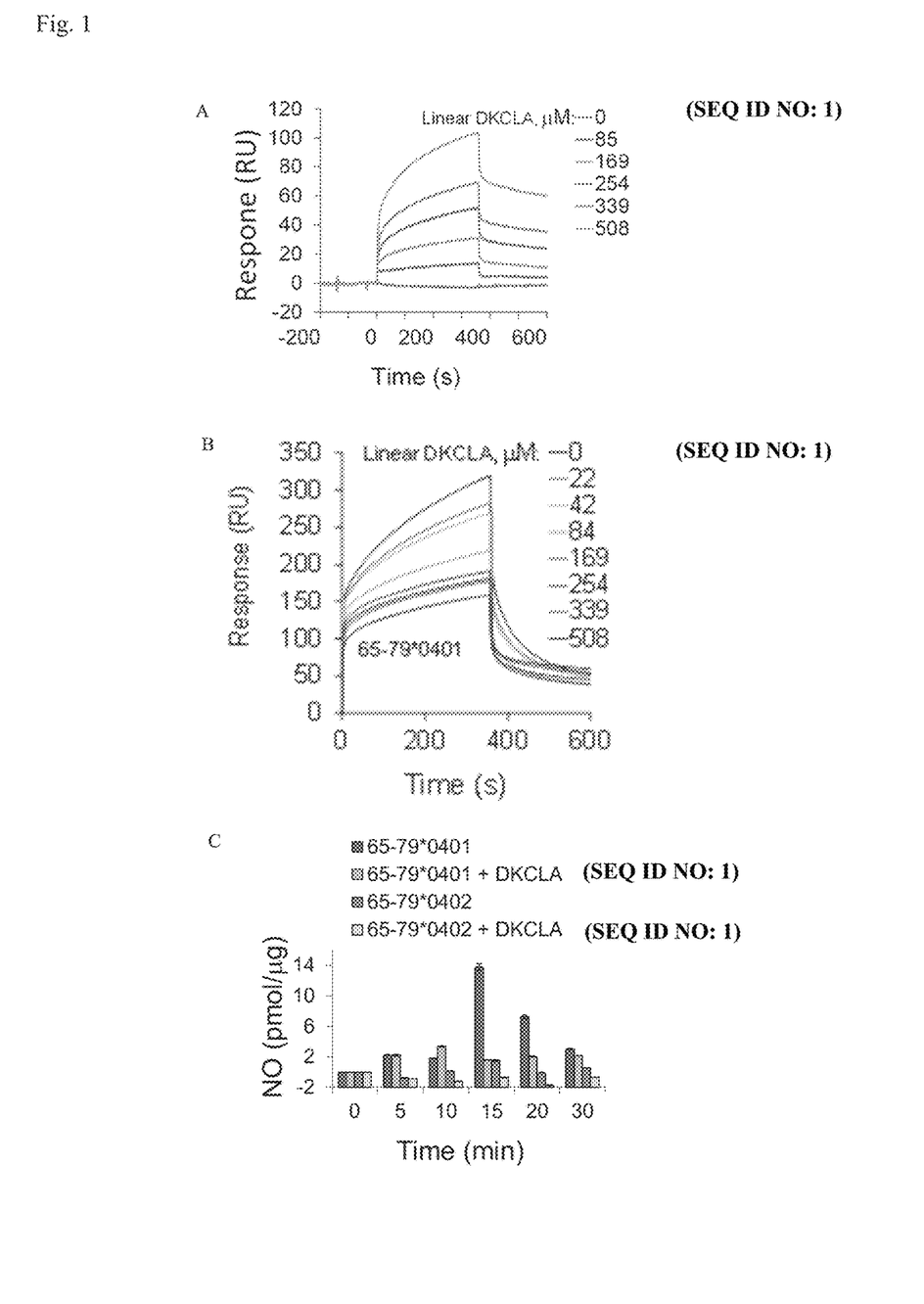
FIG. 1 shows SE-antagonistic ligand (SEAL) effects of a linear DKCLA (SEQ ID NO: 1) peptide. A. Sensorgrams showing interaction between linear DKCLA (SEQ ID NO: 1) peptide in the analyte, and recombinant CRT, chemically immobilized on the biosensor chip; B. Linear DKCLA (SEQ ID NO: 1) competitively inhibits binding of the shared eptitope (SE) ligand 65-79*0401 to CRT; C. Linear DKCLA (SEQ ID NO: 1) inhibits SE-activated NO signaling.

Screening a library of linear 5mer peptides carrying single or multiple amino acid substitutions relative to the SE consensus motif, Q/R-K/R-x-x-A (SEQ ID NO: 2), a 5mer peptide expressing the sequence DKCLA (SEQ ID NO: 1), that bound to CRT (FIG. 1A), and competitively inhibited binding of the SE ligand 65-79*0401 (a 15mer peptide corresponding to the 65-79 region coded by HLA-DRB1*04:01) (FIG. 1B) at low-μM-range IC50 potencies was identified. Linear DKCLA (SEQ ID NO: 1) also completely blocked NO induction by the SE ligand (FIG. 1C) with an $IC_{50}$ of $35\times10^{-6}$ M. Thus, these findings indicate that the linear peptide DKCLA (SEQ ID NO: 1) has a low-potency competitive inhibition effect against the SE ligand, a functional characteristic referred hereto as 'SEAL'.

DKCLA Peptidomimetics (SEQ ID NO: 1)

Figure 2:
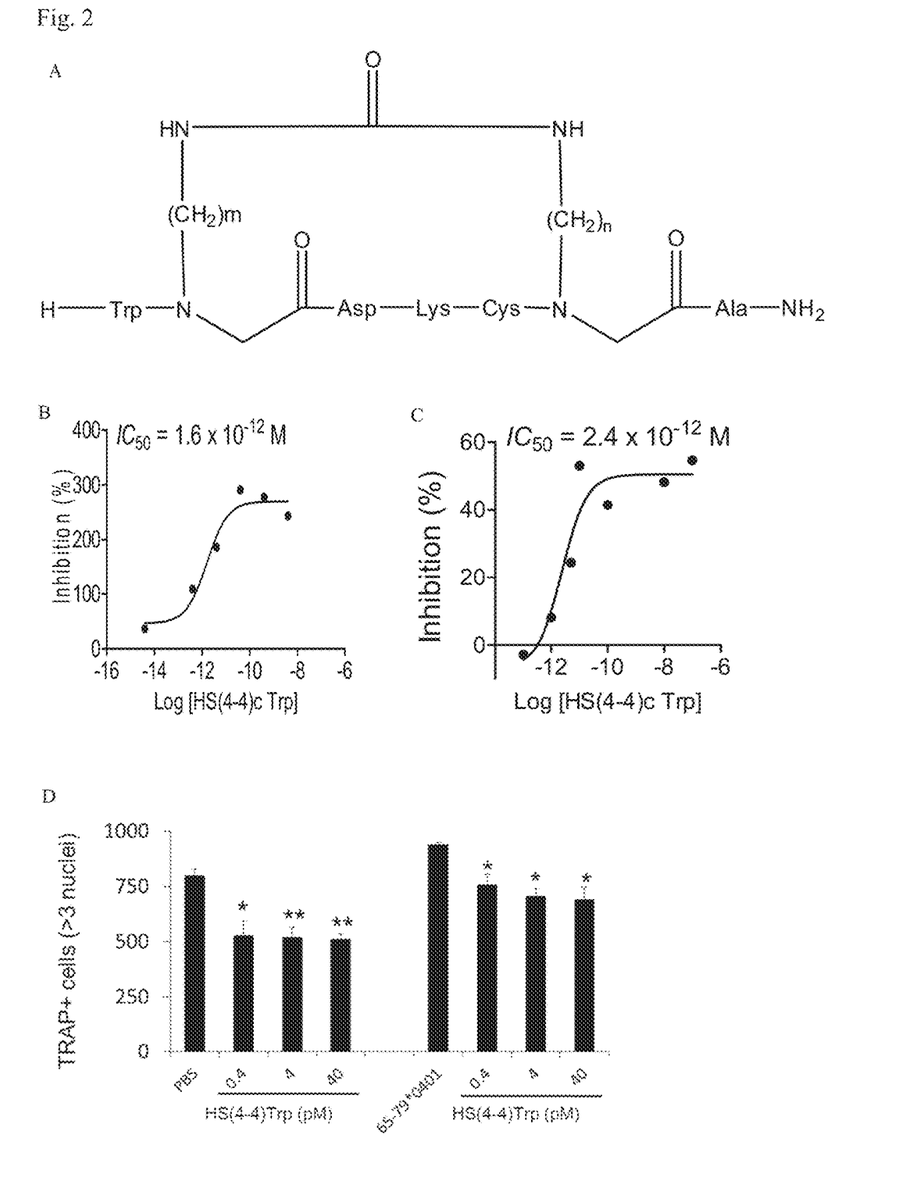
FIG. 2 shows effects of cyclic DKCLA (SEQ ID NO: 1) compounds in vitro. A. Structural formula of the cDKCLA (SEQ ID NO: 1) compound library. B. Dose-response curve of the inhibitory effect of HS(4-4)c Trp on SE-activated signaling. C. Competitive inhibition of SE ligand 65-79*0401 binding to CRT by HS(4-4)c Trp. D. HS(4-4)c Trp and HS(3-3)c Trp inhibit SE-activated osteoclastogenesis at sub-pM concentrations. E. HS(4-4)c Trp and HS(3-3)c Trp inhibit basal and SE-activated osteoclastogenesis at sub-pM concentrations in mouse bone marrow cell cultures. F. Inactive cDKCLA (SEQ ID NO: 1) analog HS(3-4)c Trp does not inhibit osteoclastogenesis.

Linear peptides are short-lived, and their biologic activity is further compromised by their random conformation in solution. Therefore, as a peptide-stabilization strategy, a library of backbone cyclic DKCLA (cDKCLA) (SEQ ID NO: 1) compounds, all carrying an identical primary sequence, but differing in terms of the cyclization linkers (FIG. 2A), was synthesized, as previously described (Naveh et al., 2012. Bioorg. Med. Chem. Lett. 22: 493-496; herein incorporated by reference in its entirety). This library was screened in signal transduction assays to determine the relative SEAL potency of individual compounds. Of the 16 analogs tested, several compounds were found to be exceptionally potent (e.g the compounds HS(4-4)c Trp, HS(3-3)c Trp and HS(6-4)c Trp, listed in Table 1), with $IC_{50}$ values as low as $1.6\times10^{-12}$ M (FIG. 2B). The inhibitory effect of compound HS(4-4)c Trp on SE-CRT interaction was tested in a cell-free SPR binding assay and was found to be a highly potent competitive inhibitor with an $IC_{50}=2.4\times10^{-12}$ M (FIG. 2C). Thus, cDKCLA (SEQ ID NO: 1) compound HS(4-4)c Trp is a 1,000,000 times more potent SEAL than the linear DKCLA (SEQ ID NO: 1) peptide.

Inhibition of Osteoclastogenesis by cDKCLA Compounds In Vitro (SEQ ID NO: 1)

One of the major hallmarks of aggressive arthritis is bone destruction, mediated by synovial OCs. It has been previously noticed that individuals carrying SE-positive HLA-DRB1 alleles have more severe bone erosions (Gonzalez-Gay et al., 2002 Semin. Arthritis Rheum. 31: 355-360; Mattey et al., 2001 Arthritis Rheum. 44: 1529-1533; Plant et al., 1998 J. Rheumatol. 25: 417-426; Weyand et al., 1994 J. Lab. Clin. Med. 124: 335-338). As discussed above, it was recently demonstrated that the SE ligand enhances OC differentiation both in vitro and in vivo (Holoshitz, 2012, J. Immunol.). Since OC play a key role in inflammatory arthritis severity, an attempt to inhibit these cells is a desirable therapeutic goal. Given the high SEAL potency of compounds HS(4-4)c Trp and HS(3-3)c Trp in signal transduction (Table 1), experiments were performed to determine their effectiveness in inhibiting OC differentiation.

As can be seen, in both human (FIG. 2D) and mouse (FIG. 2E) cells, cDKCLA (SEQ ID NO: 1) compounds were found to inhibit very efficiently SE-activated OC differentiation. Both HS(4-4)c Trp and HS(3-3)c Trp inhibited SE-activated OC differentiation at sub-pM concentrations.

Effect of SEAL In Vivo

Figure 3:
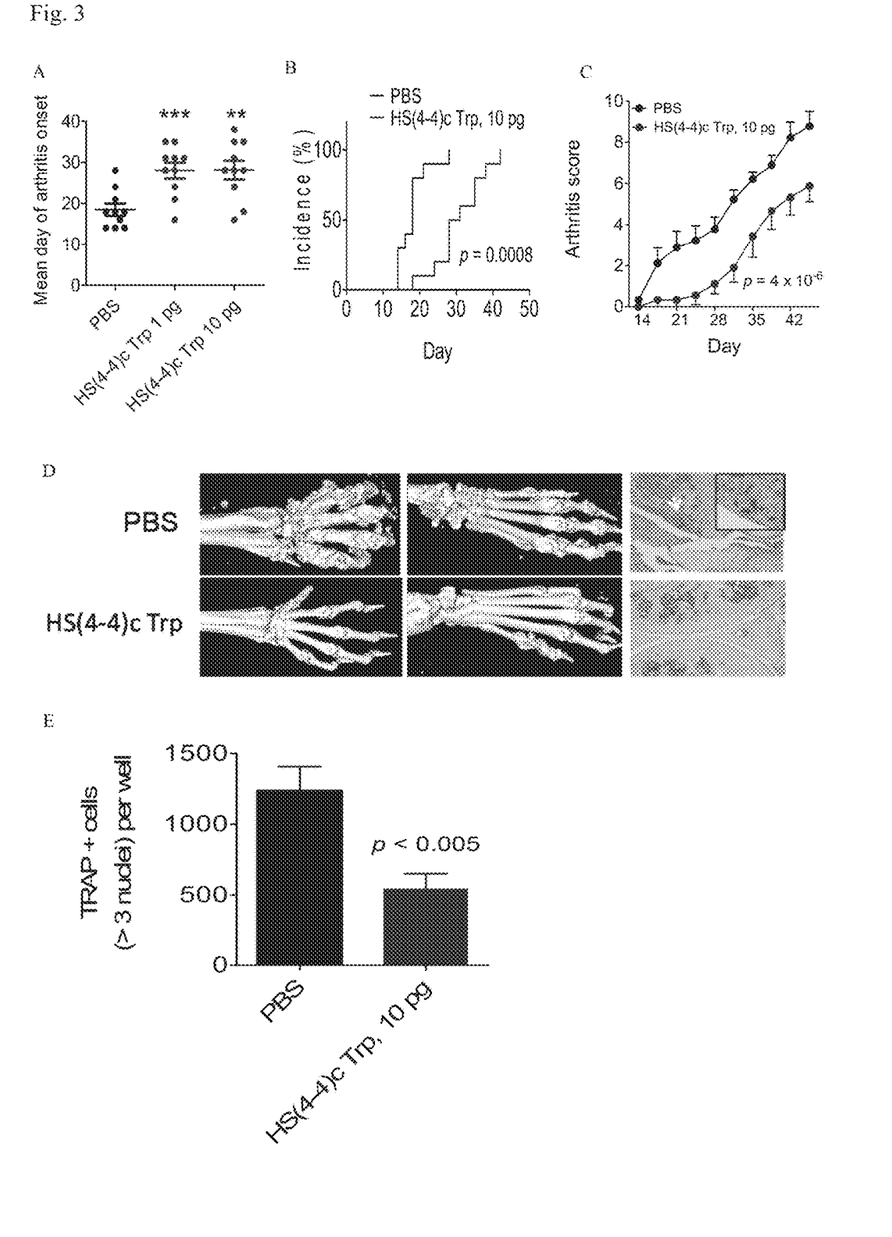
Figure 4:
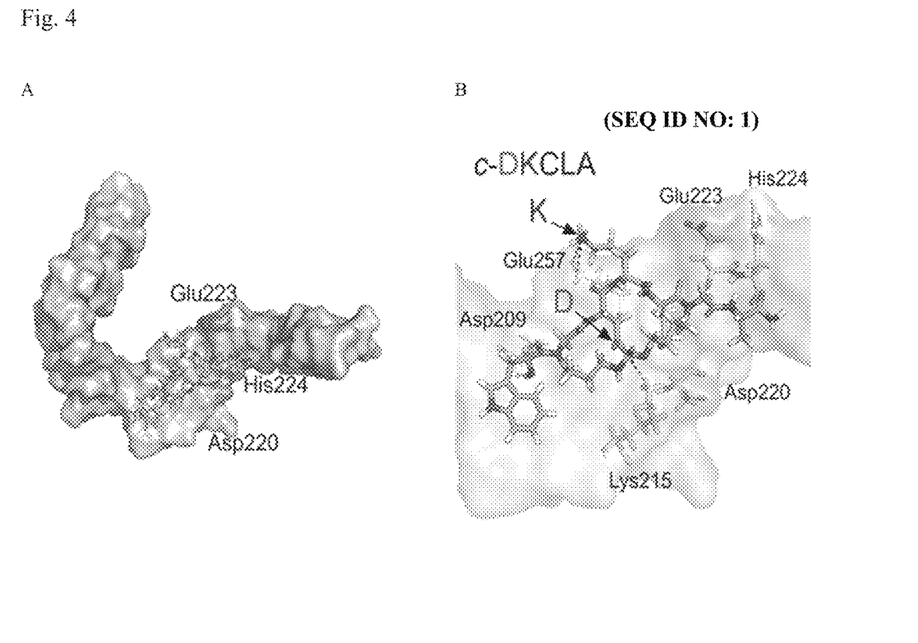
FIG. 4 shows virtual docking of cDKCLA (SEQ ID NO: 1) on the SE binding site. A. General overview of cDKCLA (SEQ ID NO: 1) on the CRT P-domain. B. Molecular interactions. Broken lines represent electrostatic bonds.

The anti-arthritis effect of the leading SEAL compound was determined in CIA. Mice injected with weekly low-pictogram doses of HS(4-4)c Trp intra-peritoneally experienced delayed onset (FIG. 3A), lower incidence (FIG. 3B), and significantly milder (FIG. 3C) arthritis. Micro-CT imaging of their joints showed lesser extent of bone destruction (FIG. 3D), and synovial tissues histology showed lower OC abundance (FIGS. 3D and 3E) in CIA mice treated with HS(4-4)c Trp. Thus, compound HS(4-4)c Trp is a potent SEAL that efficiently ameliorates erosive arthritis.

TABLE 1

Inhibition of SE-activated NO signaling.
$IC_{50}$ values of the 6 top-ranked cDKCLA (SEQ ID NO :1) compounds

| cDKCLA compound | $IC_{50}$ (M) |
| --- | --- |
| HS(4-4)c Trp | $1.6 \times 10^{-12}$ |
| HS(3-3)c Trp | $1.8 \times 10^{-12}$ |
| HS(6-4)c Trp | $6.3 \times 10^{-9}$ |
| HS(4-6)c Trp | $5.6 \times 10^{-7}$ |
| HS(6-2)c Trp | $7.7 \times 10^{-7}$ |
| HS(3-4)c Trp | $4.3 \times 10^{-6}$ | cDKCLA (SEQ ID NO: 1) competes with the SE ligand for interaction with the SE binding site on the CRT P-domain. cDKCLA (SEQ ID NO: 1) was docked against an NMR-based model of CRT P-domain (PDB ID: 1HHN) as follows: First, the binding pocket was predicted using the pipeline COACH (Yang et al., Nucleic Acids Res., 41: D1096-D1103 (2013)). COACH, a consensus-based ligand-binding site prediction program combines four template-based methods (COFACTOR (Roy et al., Nucleic Acids Res., 40:W471-W477 (2012)), TM-SITE, S-SITE, and FINDSITE (Brylinski and J. Skolnick. Proc. Natl Acad. Sci. USA, 105:129-134, (2008)), as well as ConCavity (Capra et al., PLoS Comput. Biol., 5:e1000585, (2009).). The predicted binding pocket is tethered by residues 216-225 and 255-260. Second, cDKCLA (SEQ ID NO: 1) was virtually docked on that binding site using the docking software DOCK6 (Lang et al., RNA, 15:1219-1230, (2009)).

TABLE 2

Molecular interactions between
HS(4-4)c Trp and CRT (c-DKCLA) (SEQ ID NO: 1)

| HS(4-4)c Trp component | Interacting CRT residue | Distance (Å) | Type of Interaction |
|---|---|---|---|
| NH₂ terminus of HS(4-4)c Trp | Asp209* | 1.9 | H-bond |
| HS(4-4)c Trp Ring | | | |
| D** | Lys215 | 3.8 | Electrostatic |
| K | Glu257 | 3.4 | Electrostatic |
| | | 3.7 | Electrostatic |
| C | Glu223 | <4.0 | Proximity |
| L | | | |
| A | His224 | <4.0 | Proximity |

*CRT residues are shown in a three-letter format.
**HS(4-4)c Trp amino acid residues are shown in a single-letter format.

Having fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

We claim:

1. A composition comprising a cyclic peptide, wherein said peptide has the structure:

where m and n are independently integers between 1 and 10.

2. The composition of claim 1, wherein m and n are between 2 and 8.
3. The composition of claim 1, wherein m and n are between 2 and 6.
4. The composition of claim 1, wherein m is 4 and n is 4.
5. The composition of claim 1, wherein m is 3 and n is 3.
6. The composition of claim 1, wherein m is 6 and n is 4.
7. The composition of claim 1, wherein m is 4 and n is 6.
8. The composition of claim 1, wherein m is 6 and n is 2.
9. The composition of claim 1, wherein m is 3 and n is 4.

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial sequence
<220> FEATURE:
<223> OTHER INFORMATION: Synthetic

<400> SEQUENCE: 1

Asp Lys Cys Leu Ala
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Q or R
<220> FEATURE:
<221> NAME/KEY: MISC_FEATURE
<222> LOCATION: (2)..(2)
<223> OTHER INFORMATION: Xaa = K or R
<220> FEATURE:
<221> NAME/KEY: misc_feature
<222> LOCATION: (3)..(4)
<223> OTHER INFORMATION: Xaa can be any naturally occurring amino acid

<400> SEQUENCE: 2

Xaa Xaa Xaa Xaa Ala
1               5
```

10. The composition of claim 1, wherein said composition is a pharmaceutical composition.

11. The composition of claim 10, wherein said composition comprises a pharmaceutically acceptable carrier.

12. A method of treating a bone remodeling disorder, comprising administering the composition of claim 1 to a subject.

13. The method of claim 12, wherein said subject has been diagnosed with a bone remodeling disorder.

14. The method of claim 12, wherein said bone remodeling disorder is bone destructions from rheumatoid arthritis.

15. The method of claim 14, wherein said administration treats bone destruction.

* * * * *